United States Patent
Suzuki

(10) Patent No.: US 6,485,424 B2
(45) Date of Patent: Nov. 26, 2002

(54) IMAGE FORMING METHOD AND APPARATUS, AND ULTRASONIC IMAGING APPARATUS

(75) Inventor: Yoichi Suzuki, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 43 days.

(21) Appl. No.: 09/792,171

(22) Filed: Feb. 23, 2001

(65) Prior Publication Data

US 2001/0025143 A1 Sep. 27, 2001

(30) Foreign Application Priority Data

Mar. 22, 2000 (JP) ........................................ 2000-079712

(51) Int. Cl.[7] .................................................. A61B 8/14
(52) U.S. Cl. ........................ 600/458; 600/437; 600/454
(58) Field of Search ................................. 600/437–472

(56) References Cited

U.S. PATENT DOCUMENTS

| 5,873,830 A | * | 2/1999 | Hossack et al. | ............ 600/447 |
| 5,891,037 A | * | 4/1999 | Hossack et al. | ............ 600/443 |
| 5,899,864 A | * | 5/1999 | Arenson et al. | ............ 600/453 |
| 6,030,344 A | * | 2/2000 | Guracar et al. | ............ 600/447 |

\* cited by examiner

Primary Examiner—Marvin M. Lateef
Assistant Examiner—William Jung
(74) Attorney, Agent, or Firm—Moonray Kojima

(57) ABSTRACT

In forming an image without clutters indicative of a dynamic state of an echo source containing a harmonic contrast agent based on the Doppler shift of a ultrasonic echo, the variance T of the velocity of the echo source is evaluated based on the Doppler shift, and the signal strength of the image is adjusted depending on the value of variance.

16 Claims, 9 Drawing Sheets

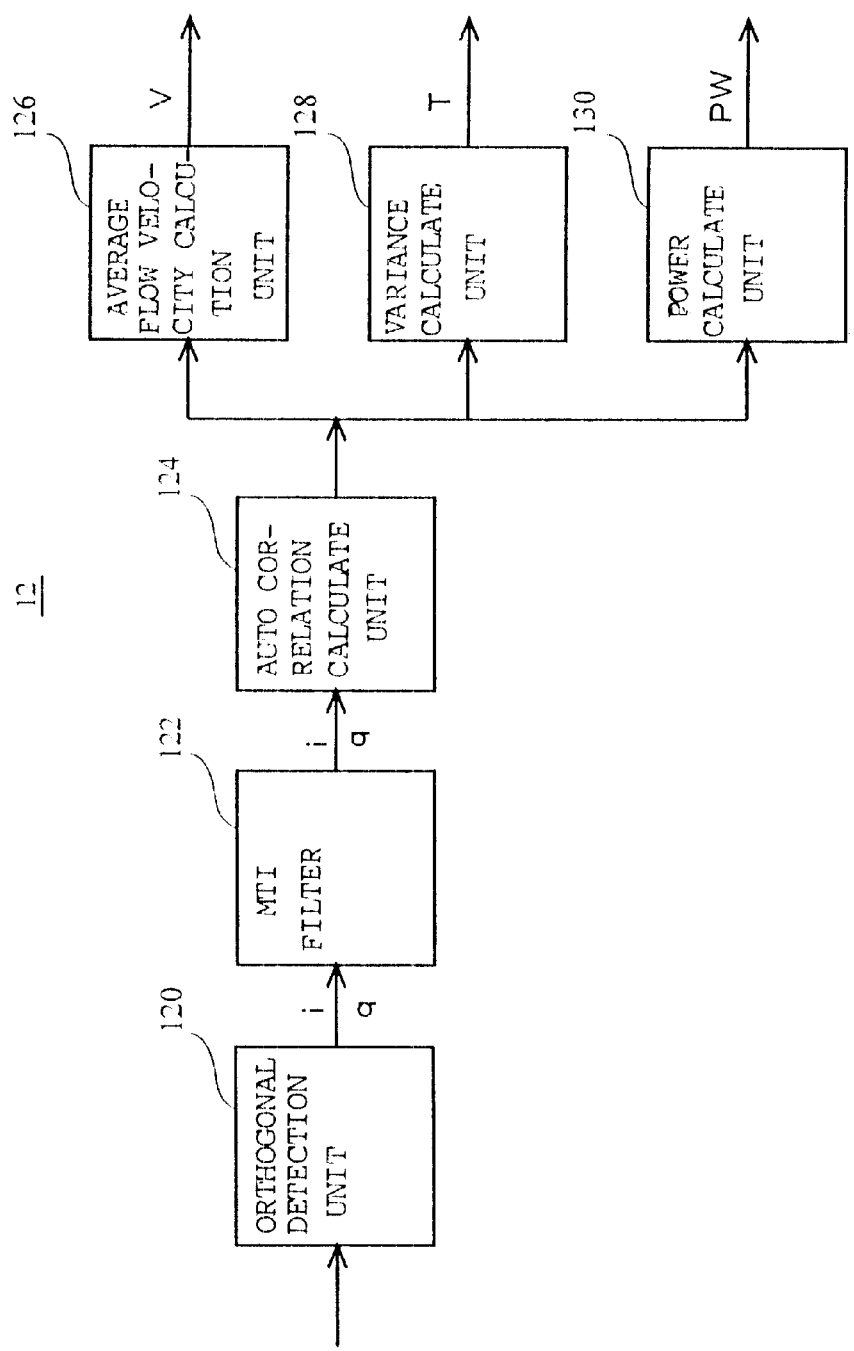

IMAGE FORMING METHOD AND APPARATUS, AND ULTRASONIC IMAGING APPARATUS

BACKGROUND OF THE INVENTION

The present invention relates to an image forming method and apparatus and a ultrasonic imaging apparatus, and particularly to an image forming method and apparatus for forming an image of a dynamic state based on the Doppler shift of a ultrasonic echo, and to a ultrasonic imaging apparatus which is equipped with t he image forming apparatus.

Ultrasonic imaging of a dynamic state of the blood flow is based on the use of the Doppler shift of a ultrasonic echo created by small particles, such as red blood cells, included in blood. The produced image is displayed as a color Doppler image.

If it is needed to raise the magnitude, of echo for the blood portion, a ultrasonic contrast agent is put in blood. The ultrasonic contrast agent is a liquid including numerous fine bubbles having a diameter of around several $\mu$m. Such contrast agent, in which fine bubbles produce an echo including the harmonics of the transmitted ultrasonic wave, is called harmonic contrast agent.

Due to the Doppler shift of a ultrasonic echo of body tissues in motion, Doppler signals which are unrelated to blood, i.e., clutters, emerge. A ultrasonic echo of body tissues further includes harmonic components due to the nonlinearity of ultrasonic transmission, and therefore clutters also emerge in the harmonic region.

Clutter's attributable to body tissues are featured to have a large power and a small velocity as compared with blood-caused signals, and this fact is utilized to separate clutters from blood-caused signals thereby to diminish the clutters. However, this scheme is not sufficient to remove clutters completely.

SUMMARY OF THE INVENTION

It is an object of the present invention is to accomplish an image forming method and apparatus capable of producing an image of dynamic state without clutters and a ultrasonic imaging apparatus which is equipped with the image forming apparatus.

Before describing a means of solving the problem, the characteristics of a ultrasonic echo which a harmonic contrast agent produces will be explained. The harmonic contrast agent is featured to have its Doppler shift exhibiting the LOC (Loss of Correlation) phenomenon, besides the creation of a harmonic echo of the transmitted ultrasonic wave.

The velocity evaluated based on the Doppler shift having the LOC phenomenon has an extremely large variance, and it can be distinguished clearly from clutters which are generally small in variance. The present invention utilizes such characteristics of the Doppler shift of the harmonic contrast agent.

(1) The invention at a first viewpoint intending to solve the above-mentioned problem resides in an image forming method which forms an image indicative of a dynamic state of an echo source containing a harmonic contrast agent based on the Doppler shift of a ultrasonic echo, and is characterized by evaluating the variance of the velocity of the echo source based on the Doppler shift, and adjusting the signal strength of the image depending on the value of variance.

The invention at this viewpoint is designed to adjust the signal strength of the image depending on the value of the variance of velocity of the echo source, and in consequence it is possible to prevent clutter elements which are generally small in variance from appearing in the image. It is also possible to emphasize the dynamic state image of the harmonic contrast agent which is generally large in variance.

(2) The invention at other viewpoint intending to solve the above-mentioned problem resides in an image forming method which forms an image indicative of a dynamic state of an echo source containing a harmonic contrast agent based on the Doppler shift of a ultrasonic echo, and is characterized by evaluating the variance of the velocity of the echo source based on the Doppler shift, and minimizing the signal strength of the image when the variance is smaller than a predetermined value.

The invention at this viewpoint is designed to minimize the signal strength of the image when the variance of the velocity of the echo source is smaller than a predetermined value, and in consequence it is possible to prevent clutter elements which are generally small in variance from appearing in the image.

(3) The invention at other viewpoint intending to solve the above-mentioned problem resides in an image forming method which forms an image indicative of a dynamic state of an echo source containing a harmonic contrast agent based on the Doppler shift of a ultrasonic echo, and is characterized by evaluating the variance of the velocity of the echo source based on the Doppler shift, and multiplying a gain, which is given as a function of the variance, to the signal strength of the image.

The invention at this viewpoint,is designed to multiply a gain, which is given as a function of the variance, to the signal strength of the image, and in consequence it is possible to prevent clutter elements which are generally small in variance from appearing in the image. It is also possible to emphasize the dynamic state image of the harmonic contrast agent which is generally large in variance.

(4) The invention at other viewpoint intending to solve the above-mentioned problem resides in an image forming method which forms an image indicative of a dynamic state of an echo source containing a harmonic contrast agent based on the Doppler shift of a ultrasonic echo, and is characterized by evaluating the variance of the velocity of the echo source based on the Doppler shift, evaluating the power of a signal having the Doppler shift, and multiplying a gain, which is given as a function of the variance and power, to the signal strength of the image.

The invention at this viewpoint is designed to multiply a gain, which is given as a function of the variance and power to the signal strength of the image, and in consequence it is possible to prevent clutter elements which are generally small in variance and large in power from appearing in the image. It is also possible to emphasize the dynamic state image of the harmonic contrast agent which is generally large in variance and small in power.

(5) The invention at other viewpoint intending to solve the above-mentioned problem resides in an image forming method of any one of the items (1) through (4), which is characterized in that the dynamic state is the velocity.

The invention at this viewpoint is capable of producing a velocity image which is rid of clutters.

(6) The invention at other viewpoint intending to solve the above-mentioned problem resides in an image forming method of any one of the items (1) through (4), which is characterized in that the dynamic state is the variance of velocity.

The invention at this viewpoint is capable of producing a variance image which is rid of clutters.

(7) The invention at other viewpoint intending to solve the above-mentioned problem resides in an image forming method of any one of the items (1) through (4), which is characterized in that the dynamic state is the combination of the velocity and variance.

The invention at this viewpoint is capable of producing a velocity/variance combination image which is rid of clutters.

(8) The invention at other viewpoint intending to solve the above-mentioned problem resides in an image forming method of any one of the items (1) through (4), which is characterized in that the dynamic state is the power of a signal having the Doppler shift.

The invention at this viewpoint is capable of producing a power image which is rid of clutters.

(9) The invention at other viewpoint intending to solve the above-mentioned problem resides in an image forming method of any one of the items (1) through (4), which is characterized in that the dynamic state is the combination of the power of a signal having the Doppler shift and the variance of velocity.

The invention at this viewpoint is capable of producing a power/variance combination image which is rid of clutters.

(10) The invention at other viewpoint intending to solve the above-mentioned problem resides in an image forming method which forms an image indicative of a dynamic state of an echo source containing a harmonic contrast agent based on the Doppler shift of a ultrasonic echo, and is characterized by evaluating the variance of the velocity of the echo source based on the Doppler shift, and forming the image based on a signal which is given as a function of the variance.

The invention at this viewpoint is designed to form an image based on a signal which is given as a function of the variance, and in consequence it is possible to prevent clutter elements which are generally small in variance from appearing in the image. It is also possible to emphasize the dynamic state image of the harmonic contrast agent which is generally large in variance.

(11) The invention at other viewpoint intending to solve the above-mentioned problem resides in an image forming method which forms an image, indicative of a dynamic state of an echo source containing a harmonic contrast agent based on the Doppler shift of a ultrasonic echo, and is characterized by evaluating the variance of the velocity of the echo source based on the Doppler shift, evaluating the power of a signal having the Doppler shift, and forming the image based on a signal which is given as a function of the variance and power.

The invention at this viewpoint is designed to form an image based on a signal which is given as a function of the variance and power, and in consequence it is possible to prevent clutter elements which are generally small in variance and large in power from appearing in the image. It is also possible to emphasize the dynamic state image of the harmonic contrast agent which is generally large in variance and small in power.

(12) The invention at other viewpoint intending to solve the above-mentioned problem resides in an image forming apparatus which forms an image indicative of a dynamic state of an echo source containing a harmonic contrast agent based on the Doppler shift of a ultrasonic echo, and is characterized by comprising a variance calculation means which evaluates the variance of the velocity of the echo source based on the Doppler shift, and a signal strength adjusting means which adjusts the signal strength of the image depending on the value of variance.

The invention at this viewpoint is designed so that the signal strength adjusting means adjusts the signal strength of the image depending on the value of the variance of velocity of the echo source, and in consequence it is possible to prevent clutter elements which are generally small in variance from appearing in the image. It is also possible to emphasize the dynamic state image of the harmonic contrast agent which is generally large in variance.

(13) The invention at other viewpoint intending to solve the above-mentioned problem resides in an image forming apparatus which forms an image indicative of a dynamic state of an echo source containing a harmonic contrast agent based on the Doppler shift of a ultrasonic echo, and is characterized by comprising a variance calculation means which evaluates the variance of the velocity of the echo source based on the Doppler shift, and a signal strength adjusting means which minimizes the signal strength of the image when the variance is smaller than a predetermined value.

The present invention at this viewpoint is designed so that the signal strength adjusting means minimizes the signal strength of the image when the variance of the velocity of the echo source is smaller than a predetermined value, and in consequence it is possible to prevent clutter elements which are generally small in variance from appearing in the image.

(14) The invention at other viewpoint intending to solve the above-mentioned problem resides in an image forming apparatus which forms an image indicative of a dynamic state of an echo source containing a harmonic contrast agent based on the Doppler shift of a ultrasonic echo, and is characterized by comprising a variance calculation means which evaluates the variance of the velocity of the echo source based on the Doppler shift, and a signal strength adjusting means which multiplies a gain, which is given as a function of the variance, to the signal strength of the image.

The invention at this viewpoint is designed so that the signal strength adjusting means multiplies a gain, which is given as a function of the variance, to the signal strength of the image, and in consequence it is possible to prevent clutter elements which are generally small in variance from appearing in the image. It is also possible to emphasize the dynamic state image of the harmonic contrast agent which is generally large in variance.

(15) The invention at other viewpoint intending to solve the above-mentioned problem resides in an image forming apparatus which forms an image indicative of a dynamic state of an echo source containing a harmonic contrast agent based on the Doppler shift of a ultrasonic echo, and is characterized by comprising a variance calculation means which evaluates the variance of the velocity of the echo source based on the Doppler shift, a power calculation means which evaluates the power of a signal having the Doppler shift, and a signal strength adjusting means which multiplies a gain, which is given as a function of the variance and power, to the signal strength of the image.

The invention at this viewpoint is designed so that the signal strength adjusting means multiplies a gain, which is given as a function of the variance and power, to the signal strength of the image, and in consequence it is possible to prevent clutter elements which are generally small in variance and large in power from appearing in the image. It is also possible to emphasize the dynamic state image of the harmonic contrast agent which is generally large in variance and small in power.

(16) The invention at other viewpoint intending to solve the above-mentioned problem resides in an image forming apparatus of any one of the items (12) through (15), which is characterized in that the dynamic state is the velocity.

The invention at this viewpoint is capable of producing a velocity image which is rid of clutters.

(17) The invention at other viewpoint intending to solve the above-mentioned problem resides in an image forming apparatus of any one of the items (12) through (15), which is characterized in that the dynamic state is the variance of velocity.

The invention at this viewpoint is capable of producing a velocity image which is rid of clutters.

(18) The invention at other viewpoint intending to solve the above-mentioned problem resides in an image forming apparatus of any one of the items (12) through (15), which is characterized in that the dynamic state is the combination of the velocity and variance.

The invention at this viewpoint is capable of producing a velocity/variance combination image which is rid of clutters.

(19) The invention at other viewpoint intending to solve the above-mentioned problem resides in an image forming apparatus of any one of the items (12) through (15), which is characterized in that the dynamic state is the power of a signal having the Doppler shift.

The invention at this viewpoint is capable of producing a power image which is rid of clutters.

(20) The invention at other viewpoint intending to solve the above-mentioned problem resides in an image forming apparatus of any one of the items (13) through (16), which is characterized in that the dynamic state is the combination of the power of a signal having the Doppler shift and the variance of velocity.

The invention at this viewpoint is capable of producing a power/variance combination image which is rid of clutters.

(21) The invention at other viewpoint intending to solve the above-mentioned problem.resides in an image forming apparatus which forms an image indicative of a dynamic state of an echo source containing a harmonic contrast agent based on the Doppler shift of a ultrasonic echo, and is characterized by comprising a variance calculation means which evaluates the variance of the velocity of the echo source based on the Doppler shift, and an image forming means which forms the image based on a signal which is given as a function of the variance.

The invention at this viewpoint is designed so that the image forming means forms an image based on a signal which is given as a function of the variance, and in consequence it is possible to prevent clutter elements which are generally small in variance from appearing in the image. It is also possible to emphasize the dynamic state image of the harmonic contrast agent which is generally large in variance.

(22) The invention at other viewpoint intending to solve the above-mentioned problem resides in an image forming apparatus which forms an image indicative of a dynamic state of an echo source containing a harmonic contrast agent based on the Doppler shift of a ultrasonic echo, and is characterized by comprising a variance calculation means which evaluates the variance of the velocity of the echo source based on the Doppler shift, a power calculation means which evaluates the power of a signal having the Doppler shift, and an image forming means which forms the image based on a signal which is given as a function of the variance and power.

The invention at this viewpoint is designed so that the image forming means forms an image based on a signal which is given as a function of the variance and power, and in consequence it is possible to prevent clutter elements which are generally small in variance and large in power from appearing in the image. It is also possible, to emphasize the dynamic state image of the harmonic contrast agent which is generally large in variance and small in power.

(23) The invention at other viewpoint intending to solve the above-mentioned problem resides in a ultrasonic imaging apparatus which transmits a ultrasonic wave, receives an echo thereof, and forms an image indicative of a dynamic state of an echo source containing a harmonic contrast agent based on the Doppler shift of the ultrasonic echo, and is characterized by comprising a variance calculation means which evaluates the variance of the velocity of the echo source based on the Doppler shift, and a signal strength adjusting means which adjusts the signal strength of the image depending on the value of variance.

The inventions at this viewpoint is designed so that the signal strength adjusting means adjusts the signal strength of the image depending on the value of the variance of velocity of the echo source, and in consequence it is possible to prevent clutter elements which are generally small in variance from appearing in the image. It is also possible to emphasize the dynamic state image of the harmonic contrast agent which is generally large in variance.

(24) The invention at other viewpoint intending to solve the above-mentioned problem resides in a ultrasonic imaging apparatus which transmits a ultrasonic wave, receives an echo thereof, and forms an image indicative of a dynamic state of an echo source containing a harmonic contrast agent based on the Doppler shift of the ultrasonic echo, and is characterized by comprising a variance calculation means which evaluates the variance of the velocity of the echo source based on the Doppler shift, and a signal strength adjusting means which minimizes the signal strength of the image when the variance is smaller than a predetermined value.

The invention at this viewpoint is designed so that the signal strength adjusting means minimizes the signal strength of the image when the variance is smaller than a predetermined value, and in consequence it is possible to prevent clutter elements which are generally small in variance from appearing in the image.

(25) The invention at other viewpoint intending to solve the above-mentioned problem resides in a ultrasonic imaging apparatus which transmits a ultrasonic wave, receives an echo thereof, and forms an image indicative of a dynamic state of an echo source containing a harmonic contrast agent based on the Doppler shift of the ultrasonic echo, and is characterized by comprising a variance calculation means which evaluates the variance of the velocity of the echo source based on the Doppler shift, and a signal, strength adjusting means which multiplies a gain, which is given as a function of the variance, to the signal strength of the image.

The invention at this viewpoint is designed so that the signal strength adjusting means multiplies a gain, which is given as a function of the variance, to the signal strength of the image, and in consequence it is possible to prevent clutter elements which are generally small in variance from appearing in the image it is also possible to emphasize the dynamic state image of the harmonic contrast agent which is generally large in variance.

(26) The invention at other viewpoint intending to solve the above-mentioned problem resides in a ultrasonic imaging apparatus which transmits a ultrasonic wave, receives an echo thereof, and forms an image indicative of a dynamic state of an echo source containing a harmonic contrast agent based on the Doppler shift of the ultrasonic echo, and is characterized by comprising a variance calculation means which evaluates the variance of the velocity of the echo source based on the Doppler shift, a power calculation means which evaluates the power of a signal having the Doppler shift, and a signal strength adjusting means which multiplies a gain, which is given as a function of the variance and power, to the signal strength of the image.

The invention at this viewpoint is designed so that the signal strength adjusting means multiplies a gain, which is given as a function of the variance and power, to the signal strength of the image, and in consequence it is possible to prevent clutter elements which are generally small in variance and large in power from appearing in the image. It is also possible to emphasize the dynamic state image of the harmonic contrast agent which is generally large in variance and small in power.

(27) The invention at other viewpoint intending to solve the above-mentioned problem resides in a ultrasonic imaging apparatus of any one of the items (23) through (26), which is characterized in that the dynamic state is the velocity.

The invention, at this viewpoint is capable of producing a velocity image which is rid of clutters.

(28) The invention at other viewpoint intending to solve the above-mentioned problem resides in a ultrasonic imaging apparatus of any one of the items (23) through (26), which is characterized in that the dynamic state is the variance of velocity.

The invention at this viewpoint is capable of producing a variance image which is rid of clutters.

(29) The invention at other viewpoint intending to solve the above-mentioned problem resides in a ultrasonic imaging apparatus of any one of the items (23) through (26), which is characterized in that the dynamic state is the combination of the velocity and variance.

The invention at this viewpoint is capable of producing a velocity/variance combination image which is rid of clutters.

(30) The invention at other viewpoint intending to solve the above-mentioned problem resides in a ultrasonic imaging apparatus of any one of the items (23) through (26), which is characterized in that the dynamic state is the power of a signal having the Doppler shift.

The invention at this viewpoint is capable of producing a power image which is rid of clutters.

(31) The invention at other viewpoint intending to solve the above-mentioned problem resides in a ultrasonic imaging apparatus of any one of the items (23) through (26) which is characterized in that the dynamic state is the combination of the power of a signal having the Doppler shift and the variance of velocity.

The invention at this viewpoint is capable of producing a power/variance combination image which is rid of clutters.

(32) The invention at other viewpoint intending to solve the above-mentioned problem resides in a ultrasonic imaging apparatus which transmits a ultrasonic wave, receives an echo thereof, and forms an image indicative of a dynamic state of an echo source containing a harmonic contrast agent based on the Doppler shift of the ultrasonic echo, and is characterized by comprising a variance calculation means which evaluates the variance of the velocity of the echo source based on the Doppler shift, and an image, forming means which forms the image based on a signal which is given as a function of the variance.

The invention, at this viewpoint is designed so that the image forming means forms an image based on a signal which is given as a function of the variance, and in consequence it is possible to prevent clutter elements which are generally small in variance from appearing in the image. It is also possible to emphasize the dynamic state image of the harmonic contrast agent which is generally large in variance.

(33) The invention at other viewpoint intending to solve the above-mentioned problem resides in a ultrasonic imaging apparatus which transmits a ultrasonic wave, receives an echo thereof, and forms an image indicative of a dynamic state of an echo source containing a harmonic contrast agent based on the Doppler shift of the ultrasonic echo, and is characterized by comprising a variance calculation means which evaluates the variance of the velocity of the echo source based on the Doppler shift, a power calculation means which evaluates the power of a signal having the Doppler shift, and an image forming means which forms the image based on a signal which is given as a function of the variance and power.

The invention at this viewpoint is designed so that the image forming means forms an image based on a signal which is given as a function of the variance and power, and in consequence it is possible to prevent clutter elements which are generally small in variance and large in power from appearing in the image. It is also possible to emphasize the dynamic state image of the harmonic contrast agent which is generally large in variance and small in power.

Therefore, the present invention can accomplish an image forming method and apparatus capable of producing a dynamic state image without clutters and a ultrasonic imaging apparatus which is equipped with the image forming apparatus.

Further objects and advantages of the present invention will be apparent from the following description of the preferred embodiments of the invention as illustrated in the accompanying invention.

BRIEF DESCRIPTION OF THE DRAWINGS

FIG. 7 is a block diagram of the doppler processing section of the apparatus shown in FIG. 1.

DETAILED DESCRIPTION OF THE INVENTION

Figure 1:
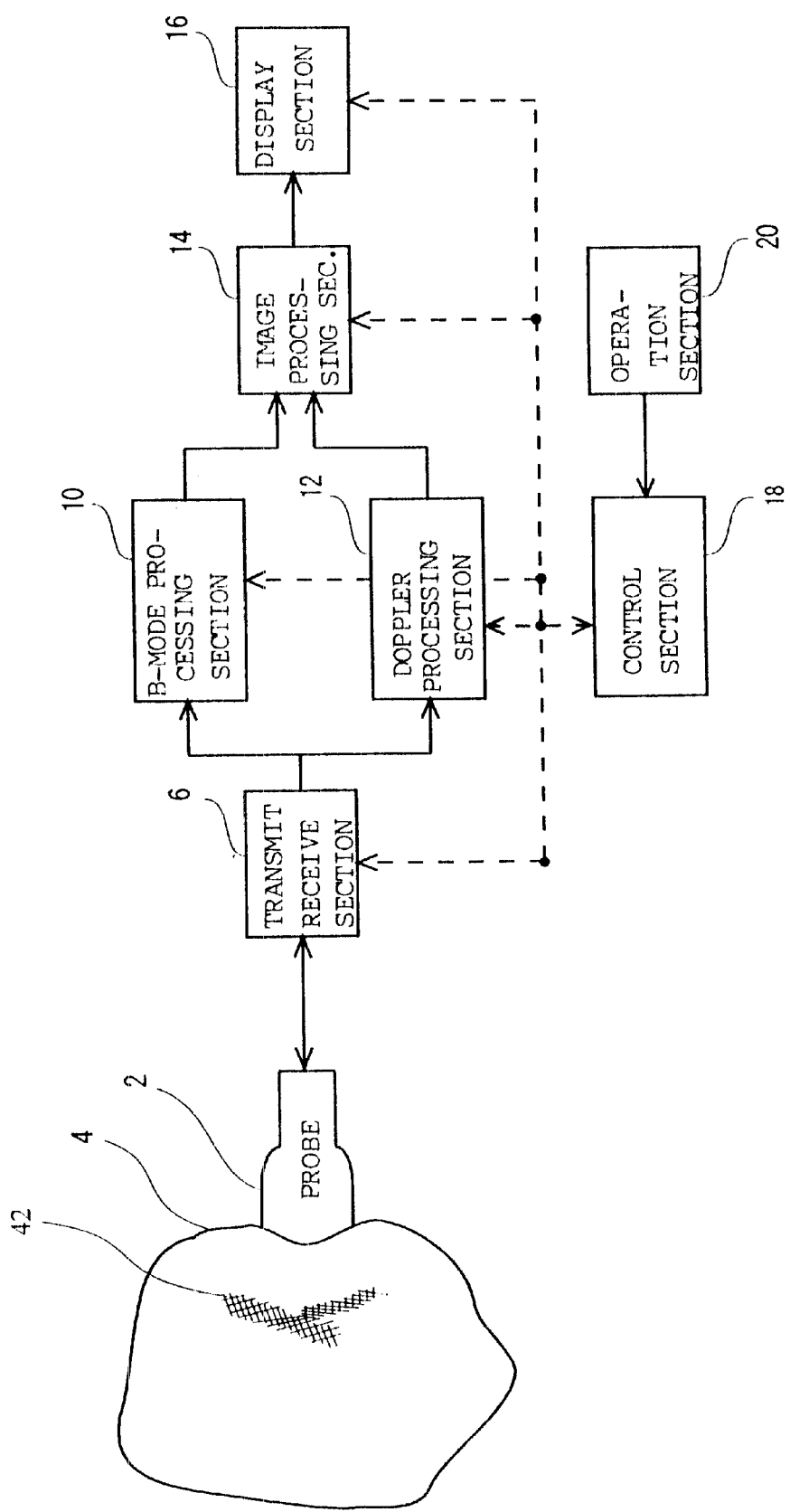
FIG. 1 is a block diagram of an apparatus which is an example of embodiment of this invention.

Embodiments of the present invention will be explained in detail with reference to the drawings. FIG. 1 shows by block diagram a ultrasonic imaging apparatus, which is an example of embodiment of this invention. The arrangement of this apparatus shows an example of embodiment the inventive apparatus. The operation of this apparatus shows an example of embodiment of the inventive method.

As shown in FIG. 1, this apparatus includes a ultrasonic probe 2. The ultrasonic probe 2 includes an array of a number of ultrasonic transducers (not shown). Each ultrasonic transducer is formed of a piezoelectric material, e.g., PZT (titanium (Ti) acid zirconium (Zr) acid) ceramics.

The ultrasonic probe 2 is used by the operator to come in contact with a subject 4. The subject 4 has in advance the injection of a ultrasonic contrast agent 42 by intravenous injection or the like. A harmonic contrast agent is used for the ultrasonic contrast agent 42.

The ultrasonic probe 2 is connected to a transmit/receive section 6. The transmit/receive section 6 supplies a drive signal to the ultrasonic probe 2, which then transmits a ultrasonic wave. The transmit/receive section 6 gets an echo signal which is received by the ultrasonic probe 2.

Figure 2:
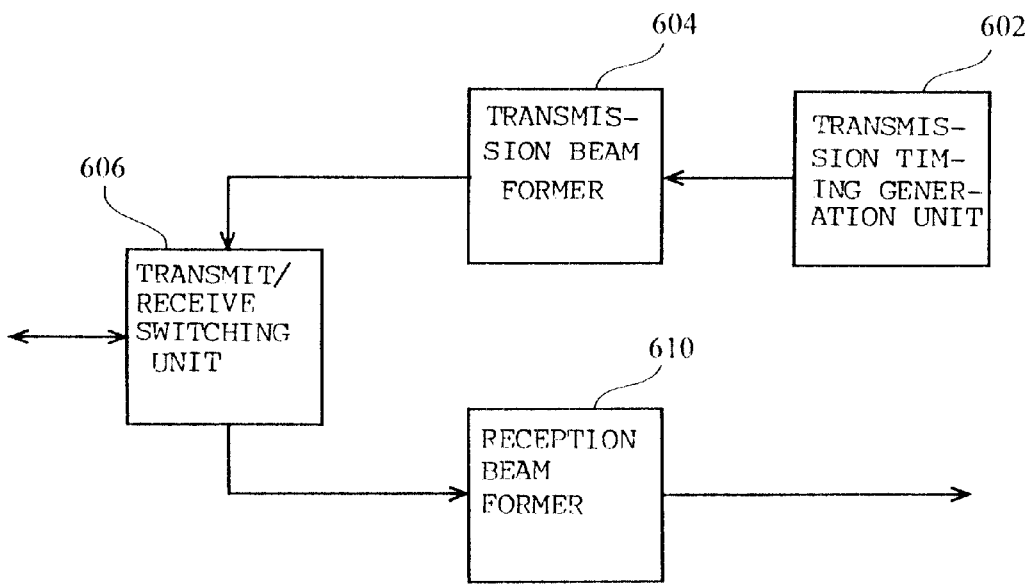
FIG. 2 is a block diagram of the transmit/receive section of the apparatus shown in FIG. 1.

FIG. 2 shows by block diagram the transmit/receive section 6. As shown in the figure, the transmit/receive section 6 includes a transmission timing generation unit 602. The transmission timing generation unit 602 generates a transmission timing signal periodically and puts the signal into a transmission beam former 604. The transmission timing signal has its period controlled by a control section 18 which will be explained later.

The transmission beam former 604, which implements the beam forming for transmission, produces a beamforming signal for making a ultrasonic beam of a prescribed azimuth based on the transmission timing signal. The beamforming signal consists of a number of drive signals having time differences which correspond to the azimuths. Beamforming is controlled by the control section 18 which will be explained later. The transmission beamformer 604 puts the transmission beamforming signal into a transmit/receive switching unit 606.

The transmit/receive switching unit 606 puts the beamforming signal into the ultrasonic transducer array. The ultrasonic transducers which constitute transmission apertures generate ultrasonic waves having phase differences which correspond to the time differences of the drive signals. Based on the wavefront composition of these ultrasonic waves, a ultrasonic beam along the line of a certain azimuth is made.

The transmit receive switching unit 606 is connected to a reception beamformer 610. The transmit/receive switching unit 606 puts the echo signals, which have been received by reception apertures of the ultrasonic transducer array into the reception beamformer 610. The reception beamformer 610, which implements the beamforming for reception in correspondence to the transmission sonic beam, makes time differences among received echoes to adjust their phases and subsequently sums the echoes to form an echo reception signal along the sonic beam of a certain azimuth. The beamforming of reception is controlled by the control section 18 which will be explained later.

Figure 3:
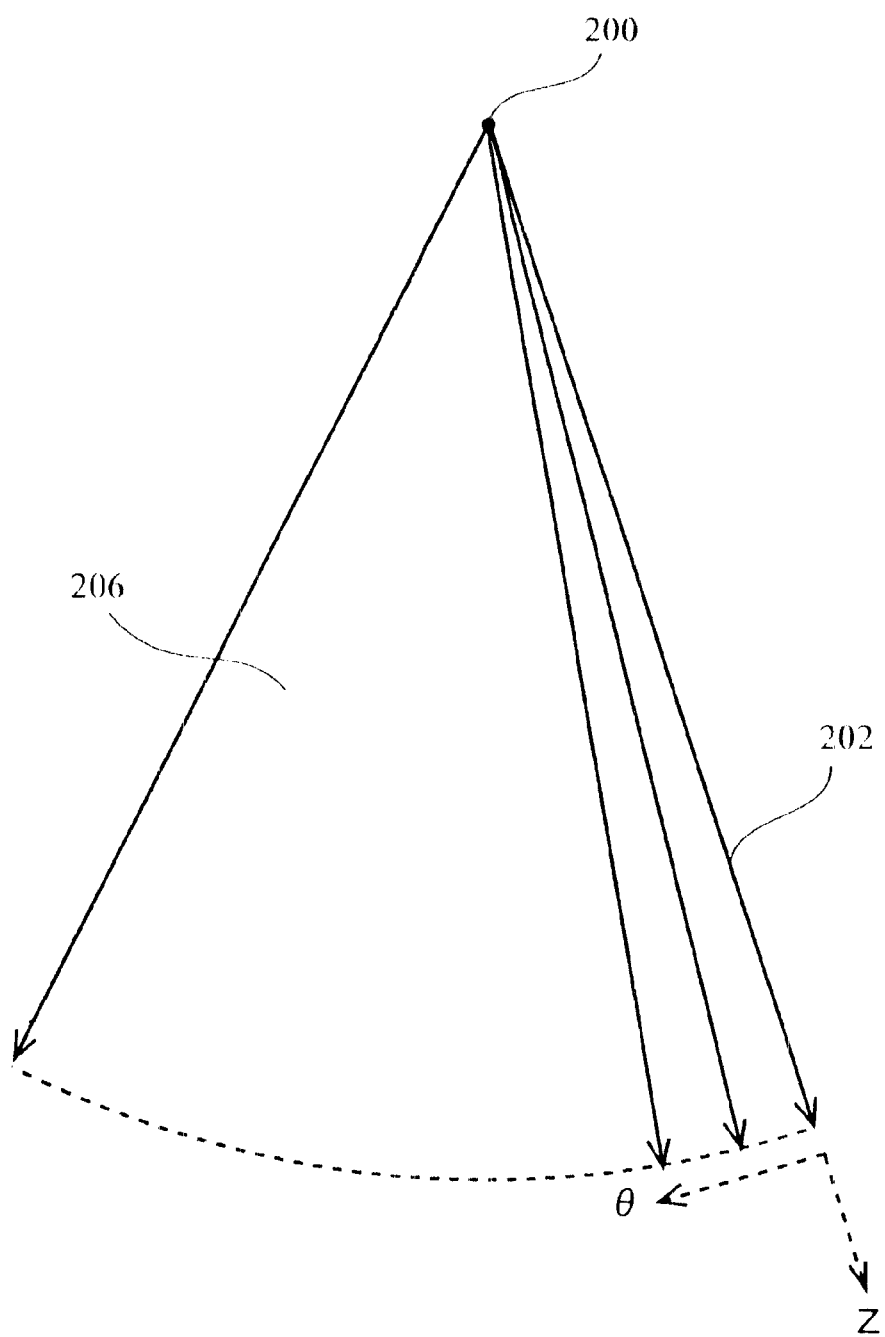
FIG. 3 is a schematic diagram of sonic beam scanning by the apparatus shown in FIG. 1.

Transmission of ultrasonic beam takes place repetitively at a certain time interval in response to the transmission timing signal generated by the transmission timing generation unit 602. In synchronism with the beam transmission, the transmission beamformer 604 and reception beamformer 610 alter the azimuth of sonic beam at a certain step. In consequence, the sonic beam scans the inside of the subject 4 in succession. The transmit/receive section 6 having this arrangement performs the scanning as shown in FIG. 3 for example. Specifically, it scans a two-dimensional sectoral region 206 along the direction of θ with a sonic beam 202 extending in the z direction from a radiation point 200, thereby performing the so-called sector scanning.

Figure 4:
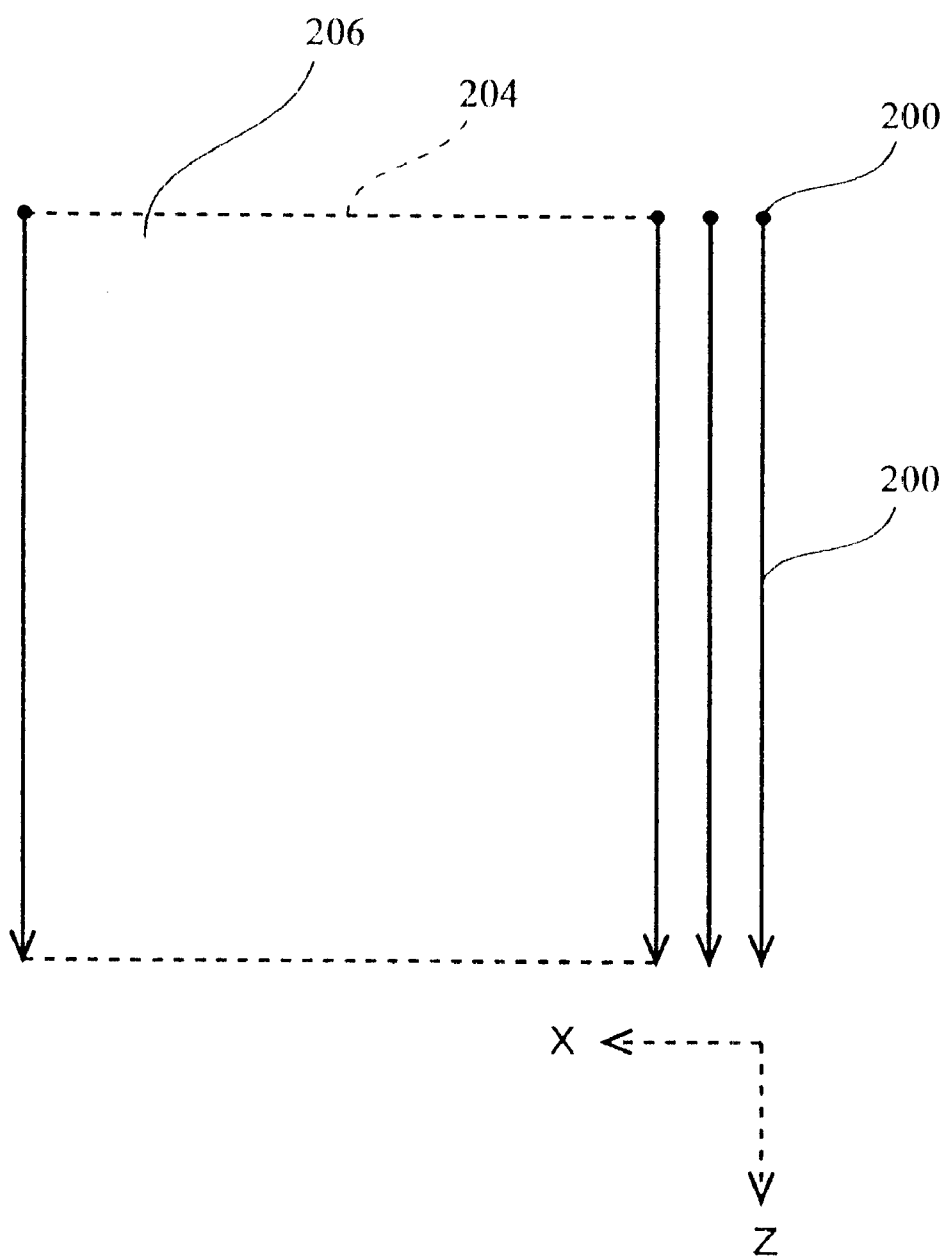
FIG. 4 is a schematic diagram of sonic beam scanning by the apparatus shown in FIG. 1.

In case the transmission and reception apertures are formed as part of the ultrasonic transducer array, the apertures are moved in succession along the array, thereby implementing the scanning as shown in FIG. 4 for example. Specifically, the sonic beam 202 which extends in the z direction from the radiation point 200 is moved along a locus 204 of straight line to scan a two-dimensional rectangular region 206 in the x direction, thereby performing the so-called linear scanning.

Figure 5:
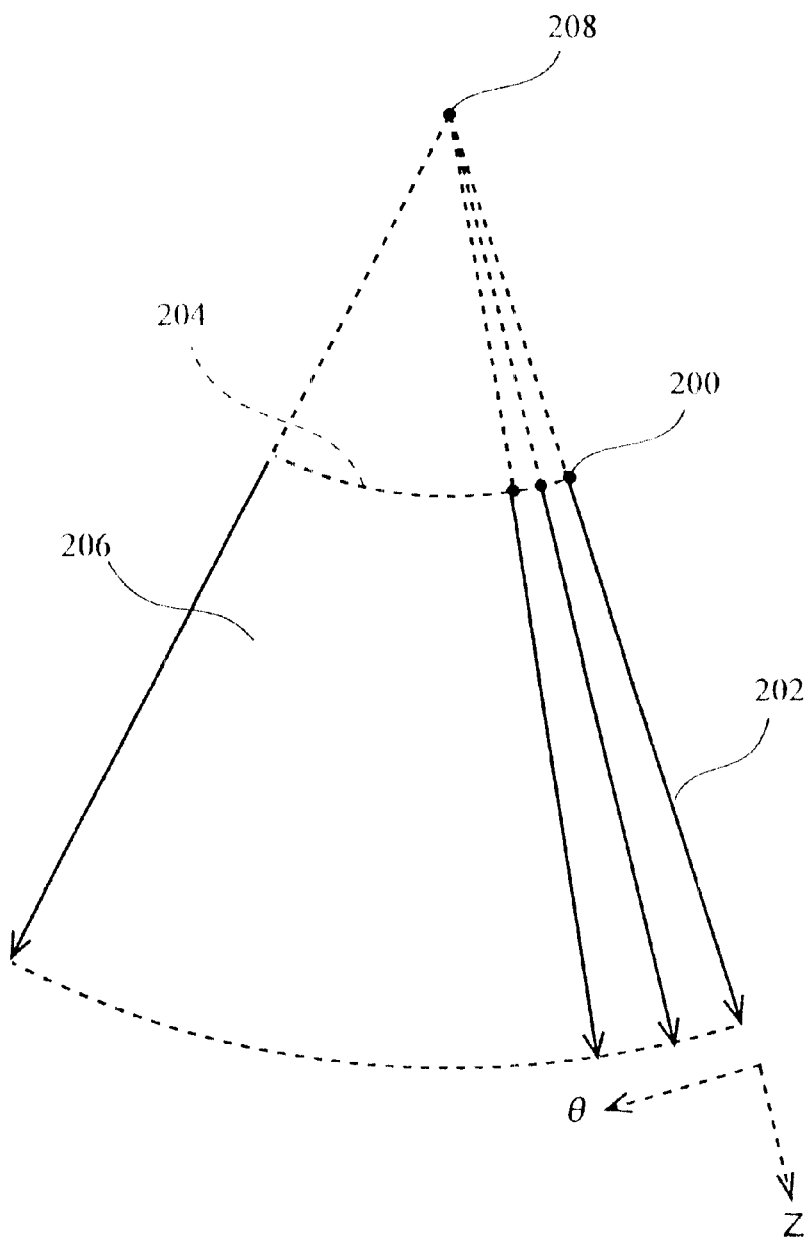
FIG. 5 is a schematic diagram of sonic beam scanning by the apparatus shown in FIG. 1.

In case the ultrasonic transducer array is a so-called convex array in which the ultrasonic transducer array is arranged along an arc which is advanced toward the ultrasonic transmission direction, it is obviously possible based on sonic beam scanning similar to linear scanning to scan a two-dimensional sectoral region 206 along the θ direction by moving the radiation point 200 of the sonic beam 202 along an circular arc locus 204 as shown in FIG. 5 for example, thereby performing the so-called convex scanning.

The transmit/receive section 6 is connected to a B-mode processing section 10 and doppler processing section 12. The echo reception signal of each sonic beam released by the transmit/receive section 6 is put into the B-mode processing section 10 and doppler processing section 12.

Figure 6:
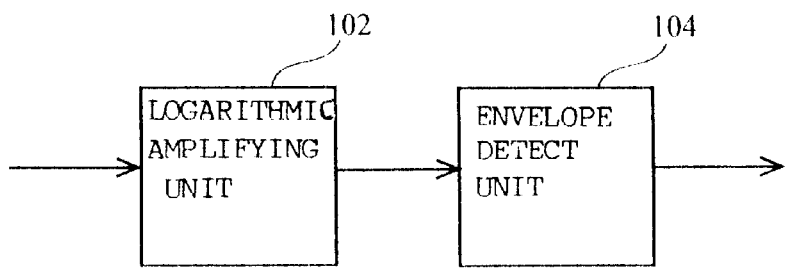
FIG. 6 is a block diagram of the B-mode processing section of the apparatus shown in FIG. 1.

The B-mode processing section 10 functions to produce B-mode image data. The B-mode processing section 10 includes a logarithmic amplify unit 102 and an envelope detect unit 104 as shown in FIG. 6. The B-mode processing section 10 implements with its envelope detect unit 104 the logarithmic amplification for the echo reception signal and implements with its envelope detect unit 104 the envelope detection for the amplified signal thereby to produce a signal indicative of the strength of echo at each reflection point on the sonicbeams, i.e., A-scope signal, and produce B-mode image data by sampling the amplitude of the A-scope signal as a value of luminous intensity.

The doppler processing section 12 functions to produce doppler image data. The doppler image data includes flow velocity data, variance data and power data which will be explained later.

The doppler processing section 12 has an orthogonal detection unit 120, an MTI (Moving Target Identification) filter 122, an autocorrelation calculation unit 124, an average flow coming toward or going away from the ultrasonic probe 2 being distinguished.

Figure 8:
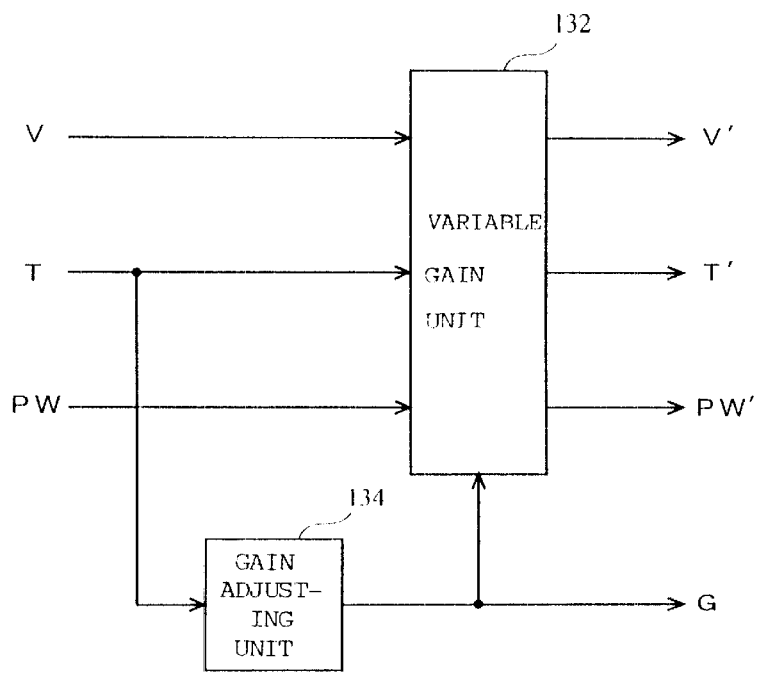
FIG. 8 is a block diagram of part of the doppler processing section of the apparatus shown in FIG. 1.

The doppler processing section 12 further includes a variable gain unit 132 as shown in FIG. 8. The variable gain unit 132 multiplies a variable gain to the flow velocity V, variance T and power PW, and delivers the resulting flow velocity V', variance T', and power PW' to the next stage.

The variable gain unit 132 has its gain adjusted by a gain adjusting unit 134. The gain adjusting unit 134, which receives the variance T as input signal, adjusts the gain of the variable gain unit 132 in accordance with the value of input signal. The section made up of the variable gain unit 132 and gain adjusting unit 134 is an example of embodiment of the inventive signal strength adjusting means.

Figure 9:
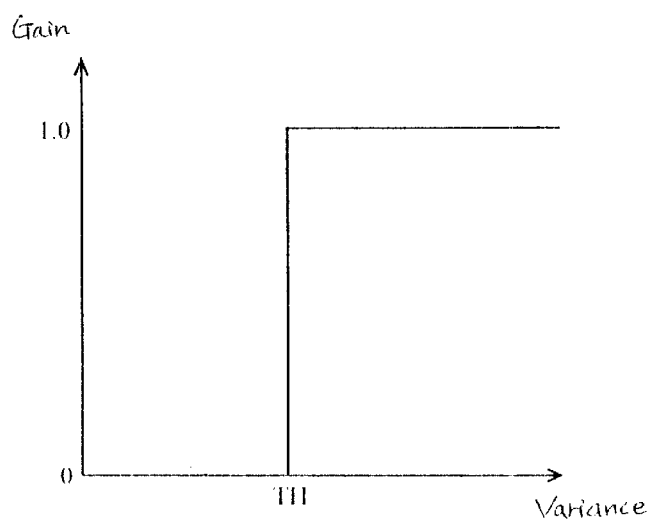
FIG. 9 is a graph showing the gain adjustment characteristics of the apparatus shown in FIG. 8.

Adjustment of gain of the variable gain unit 132 by the gain adjusting unit 134 is to have gain 1 or gain 0 depending on as to whether the variance is greater than or smaller than a certain threshold value TH, respectively, as shown in FIG. 9 for example.

In consequence, when the variance exceeds the threshold value TH, gain 1 is applied to the flow velocity V, variance T and power PW, and the input signals of the variable gain unit 132 are sent intact to the next stage. Otherwise, when the variance is smaller than the threshold value TH, gain 0 is applied to the input signals, and the signals to be sent to the next stage are all nullified. This gain adjustment is carried out for each pixel.

The threshold value TH is determined depending on the velocity calculation unit 126, a variance calculation unit 128 and a power calculation unit 130, as shown in FIG. 7.

The doppler processing section 12 implements with the orthogonal detection unit 120 the orthogonal detection for the echo reception signal and implements with the MTI filter 122 the MTI process to evaluate the Doppler shift of the echo signal. It further implements with the autocorrelation calculation unit 124 the autocorrelation calculation for the output signal of the MTI filter 122, evaluates the average of flow velocity V from the autocorrelation result with its flow velocity calculation unit 126, evaluates with the variance calculation unit 128 the variance T of the flow velocity from the result of autocorrelation calculation, and evaluates with the power calculation unit 130 the power PW of the doppler signal from the result of autocorrelation calculation. The average of flow velocity will be called simply flow velocity, the variance of velocity will be called simply variance, and the power of doppler signal will be called simply power.

The variance calculation unit 128 is an example of embodiment of the inventive variance calculation means. The power calculation unit 130 is an example of embodiment of the inventive power calculation means.

The doppler processing section 12 produces data of each sonic beam indicative of the flow velocity V, variance T and power PW of the echo source in motion in the subject 4. The data indicates the flow velocity, variance and power of each pixel on the sonic beam. The flow velocity represents the component in the sonic beam direction, with the directivity of variance value caused by the LOC phenomenon of the harmonic contrast agent. The determined threshold value TH is sufficiently greater than the variance of velocity of moving body tissues. Accordingly, based on the above-mentioned gain adjustment for the variable gain unit 132, the apparent flow velocity, variance and power caused by the motion of body tissues are not sent to the next stage. Namely, the signals are sent to the next stage while being rid of clutters.

A region with a variance greater than the threshold value TH may be given a gain greater than 1, so that the flow velocity. V, variance T and power PW indicative of the dynamic states of the harmonic contrast agent are emphasized.

Figure 10:
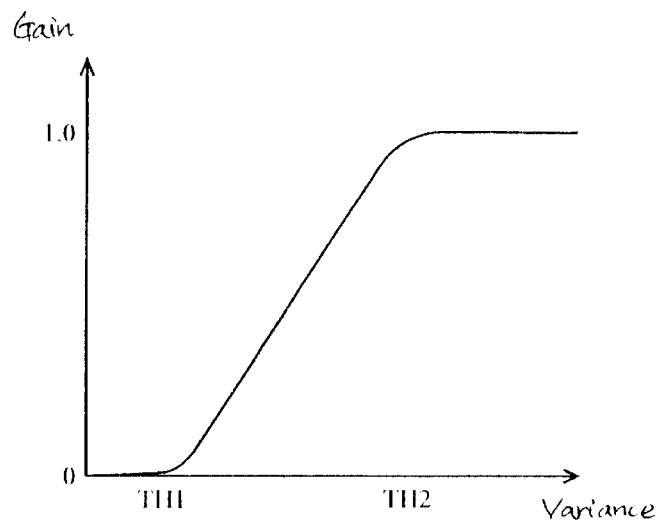
FIG. 10 is a graph showing the gain adjustment characteristics of the apparatus shown in FIG. 8.

Gain adjustment by the gain adjusting unit 134 may be continuous as a function of the variance as shown in FIG. 10, instead of the bi-level fashion described above. Specifically, the gain adjusting unit 134 provides gain 0 for a region with a variance smaller than threshold value TH1, provides gain 1 for a region with a variance greater than threshold value TH2, and varies the gain continuously from 0 to 1 for variance values between the threshold values TH1 and TH2.

The threshold value TH1 is determined to be slightly greater than the variance of clutters. The threshold value TH2 is determined to be slightly smaller than the variance of the harmonic contrast agent. Based on this gain adjustment scheme, it is possible to multiply a gain which depends on the variance value to the signals to be sent to the next stage for portions, e.g., blood flow, which do not contain the harmonic contrast agent.

The gain value G of the gain adjusting unit 134 having the characteristics shown in FIG. 9 or FIG. 10 becomes an input signal to the next stage in addition to the adjusted flow velocity V', variance T' and power PW'. The gain value G is produced for each pixel of each sonic beam. The gain value G is included in the doppler image data. The gain value G is an example of embodiment of this invention of the signal which is given as a function of the variance.

Figure 11:
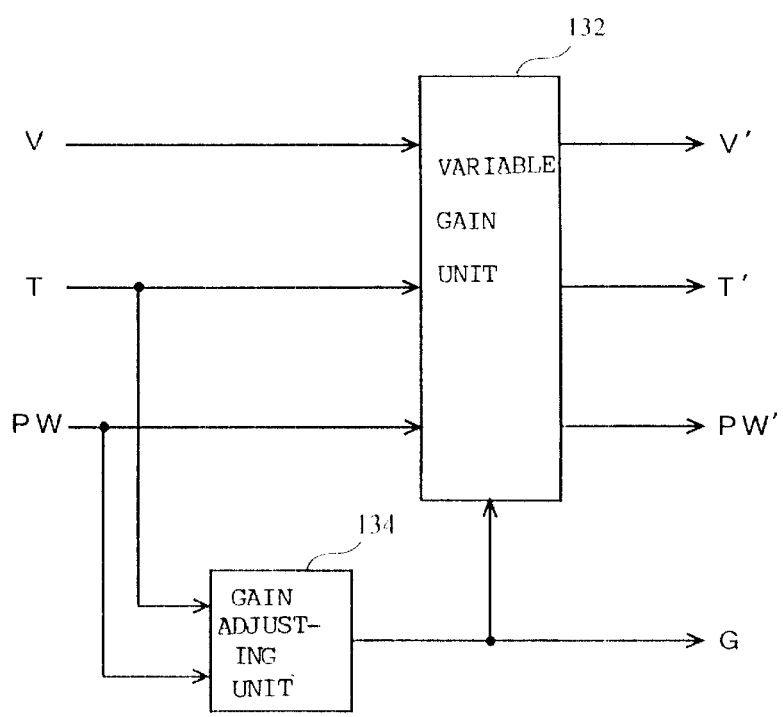
FIG. 11 is a block diagram of part of the doppler processing section of the apparatus shown in FIG. 1.

The gain adjusting unit 134 may be designed to receive the power PW as another input signal as shown in FIG. 11, so that it adjusts the gain of the variable gain unit 132 in terms of a function of the variance and power.

In this case, a region equal to or below the threshold value TH2 has its gain increased in inverse proportion to the power. Based on thins adjustment scheme, it becomes possible to make a sufficiently small gain for clutters which are generally small in variance and large in power, while multiply an appropriate gain to the signals derived from a blood flow which does not contain the harmonic contrast agent and send the resulting signals to the next stage A region of the threshold value from TH1 to TH2 may be given a gain properly. A region above the threshold value TH2 may be given a gain greater than 1, so that the flow velocity V, variance T and power PW indicative of the dynamic states of the harmonic contrast agent are emphasized.

Figure 12:
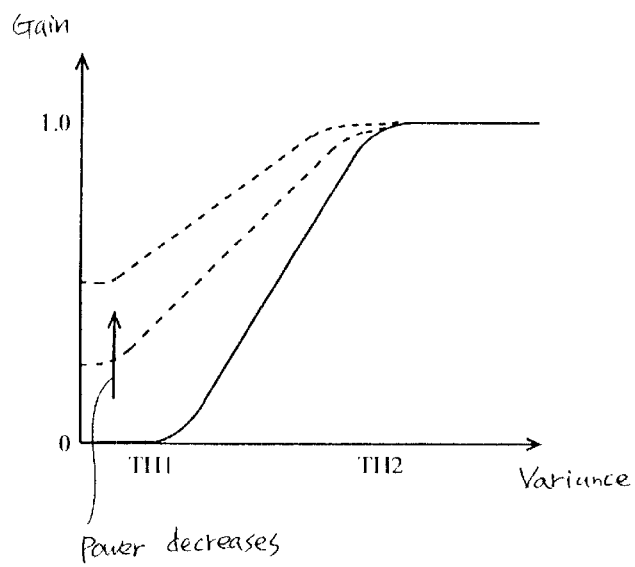
FIG. 12 is a graph showing the gain adjustment characteristics of the apparatus shown in FIG. 11.

The gain value G of the gain adjusting unit 134 having the characteristics shown in FIG. 12 becomes an input signal to the next stage in addition to the adjusted flow velocity V', variance T' and power PW'. The gain value G is produced for each pixel of each sonic beam. The gain value G is included in the doppler image data. The gain value G is an example of embodiment of this invention of the signal which is given as a function of the variance and power.

The B-mode processing section 10 and doppler processing section 12 are connected to an image processing section 14. The image processing section 14 forms a B-mode image and a doppler image based on the data provided by the B-mode processing section 10 and doppler processing section 12, respectively. The image processing section 14 is an example of embodiment of the inventive image forming means.

Figure 13:
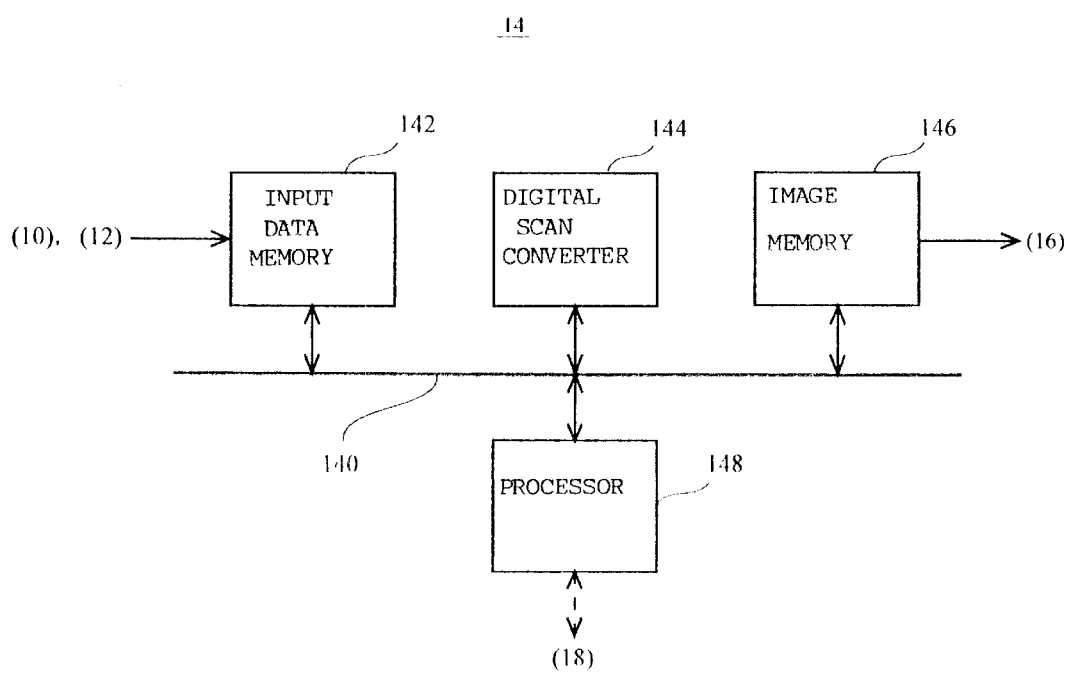
FIG. 13 is a block diagram of the image processing section of the apparatus shown in FIG. 1.

The image processing section 14 includes an input data memory 142, a digital scan converter 144, an image memory 146 and a processor 148 which are connected together by a bus 140 as shown in FIG. 13.

B-mode image data and doppier image data provided by the B-mode processing section 10 and doppler processing section 12 for each sonic beam are stored in the input data memory 142. The data in the input data memory 142 is rendered the scan conversion by the digital scan converter 144 and stored in the image memory 146. The processor 148 implements certain processings for the data in the input data memory 142 and image memory 146.

The image processing section 14 is connected with a display section 16. The display section 16 is supplied with the image signal from the image processing section 14, so that it displays a picture, based on the signal. The display section 16 is a graphic display unit which is capable of displaying a color picture.

The foregoing transmit/receive section 6, B-mode processing section 10, doppler processing section 12, image processing section 14 and display section 16 are connected with the control section 18. The control section 18 controls these sections by supplying the control signals to them. The control section 18 has inputs of various information signals from the controlled sections. The B-mode operation and doppler mode operation take place under control of the control section 18.

The control section 18 is connected with an operation section 20. The operation section 20 is operated by the operator to enter commands and information to the control section 18. The operation section 20 is an operation panel which is equipped with a keyboard, pointing device and other operation devices.

The operation of this apparatus will be explained. The operator brings the ultrasonic probe 2 to come in contact with an intended portion of the subject 4, and operates the operation section 20 to carry out the imaging operation which covers both the B mode and doppler mode for example. B-mode imaging and doppler-mode imaging take place on a time slice basis under control of the control section 18. Specifically, for example, scannings for the B mode and doppler mode take place at such a proportion as one B-mode scanning in every certain number of doppler-mode scanning.

In the B mode, the transmit/receive section 6 operates on the ultrasonic probe 2 to scan the inside of the subject 4 and receive the echo of each sonic beam. The B-mode processing section 10 amplifies with its logarithmic amplify unit 102 the echo reception signal provided by the transmit/receive section 6 and implements the envelope detection with its envelope detect unit 104 to produce the A-scope signal, thereby producing B-mode image data for each sonic beam based on the signal.

The image processing section 14 stores the B-mode image data of each sonic beam into the input data memory 142. In consequence, a sonic beam data space for the B-mode image data is formed in the input data memory 142.

In the doppler mode, the transmit/receive section 6 operates on the ultrasonic probe 2 to scan the inside of the subject 4 and receive the echo of each sonic beam. In this operation, a number of times of ultrasonic wave transmission and reception take place for each sonic beam.

The doppler processing section 12 implements with its orthogonal detection unit 120 the orthogonal detection for the echo reception signal, implements the MTI process with its MTI filter 122, and evaluates the autocorrelation with its autocorrelation calculation unit 124. It further evaluates the flow velocity V from the autocorrelation result with its flow velocity calculation unit 126, evaluates the variance T with its variance calculation unit 128, and evaluates the power PW with its power calculation unit 130. These calculated values become data indicative of the flow velocity, variance and power of the echo source of each pixel and each sonic beam.

These data yield the flow velocity V', variance T' and power PW' by being fed through the variable gain unit 132, which also provide the gain value G. The flow velocity V', variance T', power PW' and gain value G' are put into the image processing section 14 as doppler image data.

The image processing section 14 stores doppler image data of each pixel and each sonic beam provided by the doppler processing section 12 into the input data memory 142. In consequence, a sonic beam data space for each doppler image data is formed in the input data memory 142.

The processor 148 implements with its digital scan converter 144 the scan conversion for the B-mode image data and doppler image data in the input data memory 142, and writes the resulting data into the image memory 146.

In this case, the doppler image data is written as flow velocity distribution image data which is the combination of the flow velocity V' and variance T', power doppler image data with variance which is the power-doppler image data using the power PW' or the combination of the power PW' and variance T', the variance image data using the variance T', and the gain image data using the gain value G.

The processor 148 writes the B-mode image data and each doppler image data into separate areas. The display section 16 displays a picture which is based on the B-mode image data and each doppler image data.

The B-mode image becomes a tomographic image of the body tissues on the sonic, beam scanning plane. Among the color doppler images, the flow velocity distribution image becomes an image indicative of a two-dimensional distribution of flow velocities of the echo source. This image has different colors for different flow directions, has different luminous intensities for different flow velocities, and intensifies certain colors thereby to vary the purity of display colors for different variances.

The power doppler image becomes an image indicative of a two-dimensional distribution of the power of the doppler signal. This image reveals the presence of echo sources in motion. The luminous intensity in display color of the image corresponds to the power. With the variance being combined to it, certain colors are intensified thereby to vary the purity of display colors for different variances.

The variance image becomes an image indicative of a two-dimensional distribution of variance values. This image also reveals the presence of echo sources in motion. The luminous intensity in display color corresponds to the value of variance.

The gain image becomes an image indicative of a two-dimensional distribution of gains of pixels. It also reveals the presence of echo sources in motion. The luminous intensity in display color corresponds to the value of gain. In case the gain characteristics shown in FIG. 9 is used, the presence of echo sources in motion is revealed in terms of a bi-level image. In case the gain characteristics shown in FIG. 10 or FIG. 11 is used, the echo sources are revealed in terms of a tone image with saturation.

Every color doppler image is displayed by being rid of clutters and emphasized for the image of harmonic contrast agent 42 based on the gain adjustment shown in FIG. 9, FIG. 10 or FIG. 12. In consequence, the observer can know the state of doping of the harmonic contrast agent 42 in the subject 4.

The observer can know the presence of an arterial blood flow in a doped portion at an early phase of contrast agent injection. The observer can know the presence of a pylic blood flow for example in a doped portion at a mid phase of contrast agent injection. The observer can know the presence of a venous blood flow in a doped portion at a late phase of contrast agent injection.

With these images being displayed in an overlap fashion on a B-mode image on the display section 16, it is possible to observe a color doppler image which reveals clearly the positional relation with body tissues.

Many widely different embodiments of the invention may be configured without departing from the spirit and the scope of the present invention is not limited to the specific embodiments described in the specification, except as defined in the appended claims.

What is claimed is:

1. A method of forming an image indicative of a dynamic state of an echo source containing a harmonic contrast agent based on a Doppler shift of an ultrasonic echo, said method comprising the steps of:

evaluating variance of velocity of said echo source based on said Doppler shift of an image of said harmonic contrast agent; and adjusting signal strength of said image of said echo source depending on threshold value of said variance so that clutter element are prevented from occurring in the image of said echo source.

2. The method of claim 1, wherein said adjusting step comprises the step of multiplying a gain, which is given as a function of said variance, to said signal strength of said image.

3. The method of claim 2, further comprising the step of evaluating power of a signal having said Doppler shift.

4. A method of forming an image indicative of a dynamic state of an echo source containing a harmon's harmnoic contrast agent based on a Doppler shift of an ultrasonic echo, said method comprising the steps of:

evaluating variance of velocity of said echo source based on said Doppler shift of an image of said harmonic contrast agent; and forming an image of said echo source based on a signal which is depending on threshold of said variance so that clutter elements are prevented from occurring in the image of the echo source.

5. The method of claim 4, further comprising the step of evaluating power of a signal having the Doppler shift.

6. An apparatus for forming an image indicative of a dynamic state of an echo source containing a harmonic contrast agent based on a Doppler shift of an ultrasonic echo, said apparatus comprising:

first means for evaluating variance of velocity of said echo source based on said Doppler shift of an image of said harmonic contrast agent; and second means for adjusting signal strength of said image depending on threshold value of said variance so that clutter element are prevented from occurring in said image of said echo source.

7. The apparatus of claim 6, wherein said second means comprises means for multiplying a gain, which is given as a function of said variance, to said signal strength of said image.

8. The apparatus of claim 7, further comprising third means for evaluating power of a signal having said Doppler shift.

9. The apparatus of claim 7, further comprisng third means for transmitting an ultrasonic wave, and fourth means for receiving an echo thereof.

10. The apparatus of claim 8, further comprising fourth means for transmitting an ultrasonic wave, and fifth means for receiving an echo thereof.

11. The apparatus of claim 6, further comprising third means for transmitting an ultrasonic wave, and fourth means for receiving an echo thereof.

12. The apparatus of claim 6, further comprising third means for transmitting an ultrasonic wave, and fourth means for receiving an echo thereof.

13. An apparatus for forming an image indicative of a dynamic state of an echo source containing a harmonic contrast agent based on a Doppler shift of an ultrasonic echo, said apparatus comprising:

first means for evaluating variance of velocity of said echo source based on said Doppler shift of an image of said harmonic contrast agent; and second means for forming an image of said echo source based on a signal which is depending on threshold of said variance so that clutter elements are prevented from occurring in said image of said echo source.

14. The apparatus of claim 13, further comprising third means for evaluating power of a signal having said Doppler shift.

15. The apparatus of claim 13, further comprising third means for transmitting an ultrasonic wave, and fourth means for receiving an echo thereof.

16. The apparatus of claim 14, further comprising fourth means for transmitting an ultrasonic wave, and fifth means for receiving an echo thereof.

* * * * *